United States Patent
Kujundzic et al.

(10) Patent No.: US 7,342,000 B2
(45) Date of Patent: Mar. 11, 2008

(54) SEMISYNTHETIC MACROLIDE ANTIBIOTICS OF THE AZALIDE SERIES

(75) Inventors: Nedjeljko Kujundzic, Zagreb (HR); Mirjana Bukvic Krajacic, Zagreb (HR); Karmen Brajsa, Zagreb (HR)

(73) Assignee: GlaxoSmithKline istrazivacki center Zagreb, Zagreb (HR)

( * ) Notice: Subject to any disclaimer, the term of this patent is extended or adjusted under 35 U.S.C. 154(b) by 0 days.

(21) Appl. No.: 10/538,376

(22) PCT Filed: Dec. 10, 2003

(86) PCT No.: PCT/HR03/00062

§ 371 (c)(1),
(2), (4) Date: Apr. 14, 2006

(87) PCT Pub. No.: WO2004/052904

PCT Pub. Date: Jun. 24, 2004

(65) Prior Publication Data

US 2006/0252709 A1   Nov. 9, 2006

(30) Foreign Application Priority Data

Dec. 12, 2002  (HR) .................. P 20020991 A

(51) Int. Cl.
*A61K 31/70* (2006.01)
*C07H 17/08* (2006.01)

(52) U.S. Cl. .................. 514/29; 536/7.4

(58) Field of Classification Search .................. None
See application file for complete search history.

(56) References Cited

U.S. PATENT DOCUMENTS

| 4,328,334 A | 5/1982 | Kobrehel et al. |
| 4,474,768 A | 10/1984 | Bright |
| 4,492,688 A | 1/1985 | Bright |
| 6,852,702 B2 | 2/2005 | Kujundzic et al. |
| 6,872,707 B1 | 3/2005 | Marusic-Istuk et al. |

FOREIGN PATENT DOCUMENTS

| BE | 892397 | 3/1982 |
| EP | 0 132 944 | 12/1986 |
| EP | 0 316 128 | 5/1989 |
| EP | 0 657 464 | 6/1995 |
| FR | 2 473 525 | 7/1981 |
| WO | WO 97/35590 | 10/1997 |
| WO | WO 02/068438 | 9/2002 |
| WO | WO 2004/043984 | 5/2004 |
| WO | WO 2004/043985 | 5/2004 |

OTHER PUBLICATIONS

Puri, S.K., and Singh, Naresh. 2000. Azithromycin: Antimalarial Profile against Blood- and Sporozoite-Induced Infections in Mice and Monkeys. *Experimental Parasitology* 94:8-14.
Sadiq, S.T., et al. 1995. Effects of azithromycin on malariometric indices in The Gambia. *The Lancet* 346:881-882.
Kobrehel, Gabrijela, et al. 1993. 9a, 11-Cyclic Carbamates of 15-Membered Azalides. *The Journal of Antibiotics* 46(8):1239-1245.
Luger, Peter, and Maier, Roland. 1979. Molecular structure of 9-deoxy-11-deoxy-9-11-(imino(2-(2-methoxyethoxy)ethylidene)oxy)-(9S)-erythromycin, a new erythromycin derivative. *Journal of Crystal and Molecular Structure* 9(6):329-338.
Egan, Richard S., et al. 1974. Configuration of 9-Imino Derivatives of Erythromycin. *J. Org. Chem.* 39(17):2492-2494.
Kurath, P., et al. 1971. Acid Degradation of Erythromycin A and Erythromycin B. *Experientia* 27(4):362.
Djokic, Slobodan, and Tamburasev, Zrinka. 1967. Erythromycin Study: 9-amino-3-O-cladinosyl-5-0-desoaminyl-6.11,12-tryhydroxy-2,4,6,8,10,12-hexamethylpentadecame-13-olide. *Tetrahedron Letters* 17:1645-1647.
McGuire, J.M. et al. 1952. "Ilotycin," A New Antibiotic. *Antibiotics and Chemotherapy* II(6): 281-283.

*Primary Examiner*—Elli Peselev
(74) *Attorney, Agent, or Firm*—Karen L. Prus

(57) ABSTRACT

The invention relates to N'''-substituted 9a-N-(N'-carbamoyl-γ-aminopropyl), 9a-N-(N'-thiocarbamoyl-γ-aminopropyl), 9a-N-[N'-β-cyanoethyl)-N'-carbamoyl-γ-aminopropyl] and 9a-N-[N'-β-cyanoethyl)-N'-thiocarbamoyl-γ-am inopropyl] derivatives of 9-deoxo-9-dihydro-9a-aza-9a-homoerithromycin A and 5-O-desosaminyl-9-deoxo-9-dihydro-9a-aza-9a-homoerithronolide A, novel semi-synthetic macrolide antibiotics of the azalide series, of the general formula 1, wherein R represents H or cladinosyl moiety, $R^1$ represents H or β-cyanoethyl moiety, $R^2$ represents isopropyl, 1-naphtyl, 2-naphtyl, benzyl, 2-(trifluoromethyl)phenyl, 3-phenylpropyl, β-phenylethyl, ethoxycarbonyl-methyl, 1-(1-naphtyl)ethyl, 3,4,5-trimethoxyphenyl and 2,4-dichlorophenyl group, and X represents O and S, and their acceptable addition salts thereof with inorganic or organic acids, to the process for preparation of their pharmaceutical compositions as well as the use their compositions in the treatment of bacterial infections.

22 Claims, No Drawings

SEMISYNTHETIC MACROLIDE ANTIBIOTICS OF THE AZALIDE SERIES

CROSS REFERENCE TO PRIOR APPLICATION

This application is a national phase of International application Ser. No. PCT/HR2003/000062, filed Dec. 10, 2003, which was published in English as WO 2004/052904 and claims benefit of Croatian patent application Ser. No. P20020991 A, filed Dec. 12, 2002, which is hereby incorporated by reference.

TECHNICAL FIELD

Int. Cl. C 07H 17/08, A61K 31/71

Technical Problem

The present invention relates to N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A, novel semisynthetic macrolide antibiotics of the azalide series having antibacterial activity, of the general formula 1,

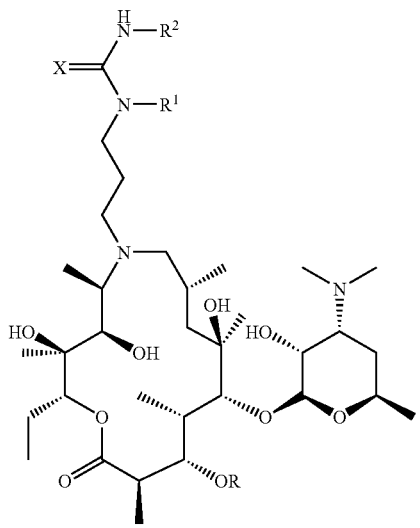

1 wherein R represents H or cladinosyl moiety, and $R^1$ represents H or β-cyanoethyl group, $R^2$ represents isopropyl, 1-naphtyl, 2-naphtyl, benzyl, 2-(trifluoromethyl)phenyl, 3-phenylpropyl, β-phenylethyl, ethoxycarbonylmethyl, 1-(1-naphtyl)ethyl, 3,4,5-trimethoxyphenyl and 2,4-dichlorophenyl group, and X represents O or S, to pharmaceutically acceptable addition salts thereof with inorganic or organic acids, to a process for the preparation of the pharmaceutical compositions as well as to the use of the pharmaceutical compositions obtained in the treatment of bacterial infections.

PRIOR ART

Erythromycin A is a macrolide antibiotic, whose structure is characterized by 14-membered macrolactone ring having carbonyl group in C-9 position. It was found by McGuire in 1952 [*Antibiot. Chemother.*, 2 (1952) 281] and for over 40 years it has been considered as a reliable and effective antimicrobial agent in the treatment of diseases caused by Gram-positive and some Gram-negative microorganisms. However, in an acidic medium it is easily converted into anhydroerythromycin A, an inactiv C-6/C-12 metabolite of a spiroketal structure [P. Kurath et al., *Experientia* 27 (1971) 362]. It is well-known that spirocyclisation of aglycone ring of erythromycin A is successfully inhibited by a chemical transformation of C-9 ketones or hydroxy groups in C-6 and/or C-12 position. By the oximation of C-9 ketones [S. Đokić et al., *Tetrahedron Lett.* 1967: 1945] and by subsequently modifying the obtained 9(E)-oxime into 9-[O-(2-methoxy-ethoxy)methyloxime]erythromycin A (ROXITHROMYCIN) [G. S. Ambrieres, Fr. pat. 2,473,525, 1981] or 9(S)-erithromycylamine [R. S. Egan et al., *J. Org. Chem.* 39 (1974) 2492] or a more complex oxazine derivative thereof, 9-deoxo-11-deoxy-9,11-{imino[2-(2-methoxy-ethoxyethylidene]oxy}-9(S)-erythromycin A (DIRITHROMYCIN) [P. Lugar et al., *J. Crist. Mol. Struct.* 9 (1979) 329], novel semisynthetic macrolides were synthetized, whose basic characteristic, in addition to a greater stability in an acidic medium, is a better pharmacokinetics and a long half-time with regard to the parent antibiotic erythromycin A. In a third way for modifying C-9 ketones use is made of Beckmann rearrangement of 9(E)-oxime and of a reduction of the obtained imino ether (G. Kobrehel et al., U.S. Pat. No. 4,328,334, 1982.) into 11-aza-10-deoxo-10-dihydroerythromycin A (9-deoxo-9a-aza-9a-homoerythromycin A) under broadening the 14-member ketolactone ring into a 15-member azalactone ring. By reductive N-methylation of 9a-amino group according to Eschweiler-Clark process (G. Kobrehel et al., BE Pat. 892,397, 1982) or by a preliminary protection of amino group by means of conversion into the coresponding N-oxides and then by alkylation and reduction [G. M. Bright, U.S. Pat. No. 4,474,768, 1984.] N-methyl-11-aza-10-deoxo-10-dihydroerythromycin A (9-deoxo-9a-methyl-9a-aza-9a-homoerithromycin A, AZITHROMYCIN) was syntetized, a prototype of azalide antibiotics, which, in addition to a broad antimicrobial spectrum including Gram-negative bacteria and intrcellular microorganisms, are characterized by a specific mechanism of transport to the application site, a long biological half-time and a short therapy period. In EP A 0316128 (Bright G. M. et al.) novel 9a-allyl and 9a-propargyl derivatives of 9-deoxo-9a-aza-9a-homoerythromycin A are disclosed and in U.S. Pat. No. 4,492,688, from 1985 (Bright G. M.) the synthesis and the antibactertial activity of the corresponding cyclic ethers are disclosed. In the there are further disclosed the syntesis and the activity spectrum of novel 9-deoxo-9a-aza-11-deoxy-9a-homoerythromycin A 9a,11-cyclic carbamates and O-methyl derivatives thereof (G. Kobrehel et al., *J. Antibiot.* 46 (1993) 1239-1245).

By reaction of 9-deoxo-9-dihydro-9a-aza-9a-homoerithromycin A with isocyanates or isothiocyanates respectively [N. Kujundžić et al. Croat. Pat. 931480, 1993.], 9a-N-(N'-carbamoyl) and 9a-N-(N'-thiocarbamoyl) derivatives of 9-deoxo-9-dihydro-9a-aza-9a-homoerithromycin A with a certian antibacterial activity are obtained.

According to the known and established Prior Art, N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A and pharmaceutically acceptable addition salts thereof with inorganic or organic acids, a process for the preparation thereof as well as the preparation methods and use an pharmaceutical preparations have not been disclosed as yet.

It has been found and it is object of the present invention, that N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A, novel semisinthetic macrolide antibiotic of the azalide series and pharmaceutically acceptable addition salts thereof with inorganic or organic acids, may be prepared by reacting 9a-N-(γ-aminopropyl) and 9a-N-[N'-(β-cyanoethyl)-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A with isocyanates or isothiocyanates and optionally by reacting the obtained N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A with organic and inorganic acids.

Technical Solution

It has been found that novel N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A of the general formula 1,

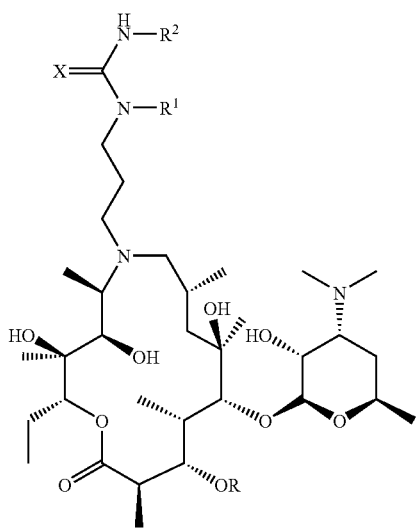

1 wherein R represents H or cladinosyl group, R¹ represents H or β-cyanoethyl moiety, R² represents isopropyl, 1-naphtyl, 2-naphtyl, benzyl, 2-(trifluoromethyl)phenyl, 3-phenylpropyl, β-phenylethyl, ethoxycarbonylmethyl, 1-(1-naphtyl) ethyl, 3,4,5-trimethoxyphenyl and 2,4-dichlorophenyl group, and X represents O or S, and their acceptable addition salts there of with inorganic or organic acids, may be prepared by reacting 9a-N-(β-aminopropyl) and 9a-N-[N'-(β-cyanoethyl)-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A general formula 2,

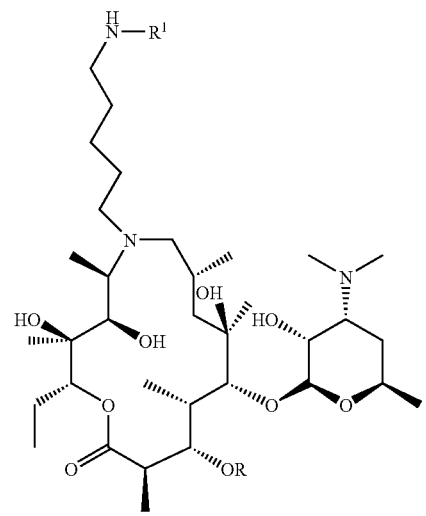

2 wherein R represents H or cladinosyl group and R¹ represents H or β-cyanoethyl moiety, with isocyanates or thioisocyanates general formula 3, $$R^2-N=C=X \qquad 3$$

wherein R² and X have above meanings, in toluene, xylene or some other aprotic solvent, at a temperature 0° to 110° C.

Pharmaceutically acceptable acid addition salts, which also represent an object of present invention, were obtained by reaction N"-substituted 9a-N-(N'-carbamoyl-γ-aminopropyl), 9a-N-(N'-thiocarbamoyl-γ-aminopropyl), 9a-N-[N'(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A with an at least equimolar amount of the corresponding inorganic or organic acid such as hydrochloric acid, hydroiodic acid, sulfuric acid, phosphoric acid, acetic acid, trifluoroacetic acid, propionic acid, benzoic acid, benzenesulfonic acid, methane sulfonic acid, laurylsulfonic acid, stearic acid, palmitic acid, succinic acid, ethylsuccinic acid, lactobionic acid, oxalic acid, salicylic acid and similar acid, in a solvent inert to the reaction. Addition salts are isolated by evaporating the solvent or, alternatively, by filtration after a spontaneous precipitation or a precipitation by the addition of a non-polar cosolvent.

N"-Substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A of the general formula 1 and pharmaceutically acceptable addition salts with inorganic or organic acids thereof possess an antibacterial activity in vitro.

Minimal inhibitory concentration (MC) is defined as the concentration which shows 90% growth inhibition, and was determinated by broth dilution methods National Committe for Clinical Laboratory Standards (NCCLS, M7-A2 protocols). Final concentration of test substances were in range from 64 to 0.125 mg/l. MIC levels for all compound were determinated on panel of susceptible, and resistant Gram positive bacterial strains (*S. aureus, S. pneumoniae* and *S. pyogenes*) and on Gram negative strains (*E. coli, H. influenzae, E. faecalis, M. catarrhalis*).

It is evident from Table 1 and Table 2 that standard strains are susceptible to newly synthetized compounds of general formula 1. Thus they may be used as therapeutic agents in the treatment of invective diseases in animals, especially mammals and humans, caused by a broad spectrum of Gram-positive and Gram-negative bacteria, mycoplasmas and generally patogenic microorganisms that are susceptible to the compounds of the formula 1. To this purpose the above compounds and pharmaceutically acceptable acid addition salts thereof may be administered orally in usual doses from 0.2 mg/kg body weight daily to about 250 mg/kg/day, most preferably from 0.5-50 mg/kg/day, or parenterally in the form of subcutaneous and intramuscular injections.

Process for the preparation of N"-substituted 9a-N-(N'-carbamoyl-γ-aminopropyl), 9a-N-(N'-thiocarbamoyl-γ-aminopropyl), 9a-N-[N'-(β-cyanoethyl)-N'-carbamoyl-γ-aminopropyl] and 9a-N-[N'-(β-cyanoethyl)-N'-thiocarbamoyl-γ-aminopropyl] derivatives of 9-deoxo-9-dihydro-9a-aza-9a-homoerithromycin A and 5-O-desosaminyl-9-deoxo-9-dihydro-9a-aza-9a-homoerithronolide A of this invention is illustrated by the following Examples which should in no way be construed as a limitation of the scope thereof.

TABLE 1

Antibacerial in vitro activity of novel N"-substituted 9a-N-(N'--carbamoyl-γ-aminopropyl) and 9a-N-(N'-thiocarbamoyl-γ-aminopropyl) derivatives of 9-deoxo-9-dihydro-9a-aza-9a-homoerithromycin A presented as MIC values in comperison with erythromycin A (Er).

| Test organisms | MIK µg/ml Compound from example | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12* | Er |
| *S. aureus* ATCC 13709 | 2 | 0.5 | 0.5 | 2 | 2 | 2 | 1 | 1 | 8 | 16 | 4 | 8 | ≦0.125 |
| *S. pneumoniae* | ≦0.125 | ≦0.125 | ≦0.125 | ≦0.125 | ≦0.125 | ≦0.125 | ≦0.125 | ≦0.125 | 8 | ≦0.125 | 16 | ≦0.125 | |
| *S. pyogenes* | ≦0.125 | ≦0.125 | ≦0.125 | ≦0.125 | ≦0.125 | ≦0.125 | ≦0.125 | ≦0.125 | ≦0.125 | ≦0.125 | ≦0.125 | ≦0.125 | 0.25 |
| *S. pyogenes* iMLS | 8 | 2 | 4 | 2 | 4 | 8 | 4 | 4 | 16 | 8 | 32 | 2 | >64 |
| *S. pyogenes* M | 32 | 4 | 8 | 4 | 4 | 32 | 8 | 8 | 64 | 16 | 64 | 8 | 8 |
| *M. catarrhalis* ATCC 23246 | 0.5 | 0.25 | 1 | 1 | 2 | 8 | 1 | 1 | 4 | 4 | 16 | 0.5 | — |
| *H. influenzae* ATCC 49247 | 32 | 1 | 2 | 2 | 2 | 16 | 2 | 2 | 32 | 2 | 16 | 2 | 2 |
| *E. faecalis* ATCC 29212 | 32 | 4 | 16 | 8 | 4 | 64 | 16 | 16 | >64 | 16 | >64 | 8 | 1 |
| *E. coli* ATCC 25922 | 16 | 8 | 16 | 16 | 8 | 32 | 16 | 32 | >64 | 64 | >64 | 32 | 32 |

TABLE 2

Antibacerial in vitro activity of novel N"-substituted 9a-N-[N'-(β--cyanoethyl)-N'-carbamoyl-γ-aminopropyl] and 9a-N-[N'-(β-cyanoethyl)-N'--thiocarbamoyl-γ-aminopropyl] derivatives of 9-deoxo-9-dihydro-9a-aza-9a--homoerithromycin A presented as MIC values in comperison with erythromycin A (Er).

| Test organisms | MIK µg/ml Compound from example | | | | | | | | | | | | |
|---|---|---|---|---|---|---|---|---|---|---|---|---|---|
| | 27 | 28 | 29 | 30 | 31 | 32 | 33 | 34 | 36 | 37 | 38 | 39* | Er |
| *S. aureu* ATCC 13709 | 4 | 1 | 2 | 1 | 4 | 4 | 1 | 1 | 2 | 4 | 1 | 1 | ≦0.125 |
| *S. pneumoniae* ATCC | ≦0.125 | ≦0.125 | ≦0.125 | ≦0.125 | ≦0.125 | ≦0.125 | ≦0.125 | ≦0.125 | ≦0.125 | ≦0.125 | ≦0.125 | ≦0.125 | ≦0.125 |
| *S. pyogenes* ATCC | ≦0.125 | ≦0.125 | ≦0.125 | ≦0.125 | ≦0.125 | ≦0.125 | ≦0.125 | ≦0.125 | ≦0.125 | ≦0.125 | ≦0.125 | ≦0.125 | 0.25 |
| *S. pyogenes* iMLS | 8 | 2 | 16 | 2 | 4 | 8 | 4 | 4 | 8 | 47 | 2 | 32 | >64 |
| *S. pyogenes* M | 32 | 4 | 64 | 4 | 4 | 32 | 8 | 8 | 16 | 8 | 8 | 64 | 8 |
| *M. catarrhalis* ATCC 23246 | 0.5 | 0.25 | 4 | 1 | 2 | 8 | 1 | 1 | 4 | 1 | 0.5 | 16 | — |
| *H. influenzae* ATCC 49247 | 32 | 1 | 32 | 2 | 2 | 16 | 2 | 2 | 2 | 2 | 2 | 16 | 2 |
| *E. faecalis* ATCC 29212 | 32 | 4 | >64 | 8 | 4 | 64 | 16 | 16 | 16 | 16 | 8 | >64 | 1 |
| *E. coli* ATCC 25922 | 16 | 8 | >64 | 16 | 8 | 32 | 16 | 32 | 64 | 16 | 32 | >64 | 32 |

EXAMPLE 1

9-Deoxo-9-dihydro-9a-N-(N'-isopropylcarbainoyl-γ-aminopropyl)-9a-aza-9a-homoerythromycin A A mixture of 1.0 g (1.26 mmol) 9-deoxo-9-dihydro-9a-aza-9a-(γ-aminopropyl)-9a-homoerythromycin A and 0.1 g (1.3 mmol) of isopropylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:amnmonia=90:9:1.5, pure 9-deoxo-9-dihydro-9a-N-(N'-isopropylcarbamoyl-γ-aminopropyl)-9a-aza-9a-homoerythromycin A was obtained.

MS(ES$^+$)m/z=877.

EXAMPLE 2

9-Deoxo-9-dihydro-9a-N-[N'-(1-naphtyl)carbamoyl-γ-aminopropyl]-9a-aza-9a-homoerythromycin A A mixture of 1.0 g (1.26 mmol) 9-deoxo-9-dihydro-9a-aza-9a-(γ-aminopropyl)-9a-homoerythromycin A and 0.22 g (1.26 mmol) of 1-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(1-naphtyl)carbamoyl-γ-aminopropyl]-9a-aza-9a-homoerythromycin A was obtained.

MS(ES$^+$)m/z=961.

EXAMPLE 3

9-Deoxo-9-dihydro-9a-N-(N'-benzylcarbamoyl-γ-aminopropyl)-9a-aza-9a-homoerythromycin A A mixture of 1.0 g (1.26 mmol) 9-deoxo-9-dihydro-9a-aza-9a-(γ-aminopropyl)-9a-homoerythromycin A and 0.17 g (1.3 mmol) of benzylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-(N'-benzylcarbamoyl-γ-aminopropyl)-9a-aza-9a-homoerythromycin A was obtained.

MS(ES$^+$)m/z=925.

EXAMPLE 4

9-Deoxo-9-dihydro-9a-N-(N'-benzylthiocarbamoyl-γ-aminopropyl)-9a-aza-9a-homoerythromycin A A mixture of 1.0 g (1.26 mmol) 9-deoxo-9-dihydro-9a-aza-9a-(γ-aminopropyl)-9a-homoerythromycin A and 0.17 g (1.3 mmol) of benzylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-(N'-benzyltiocarbamoyl-γ-aminopropyl)-9a-aza-9a-homoerythromycin A was obtained.

MS(ES$^+$)m/z=941.

EXAMPLE 5

9-Deoxo-9-dihydro-9a-N-[N'-(1-naphtyl)thiocarbarmoyl-γ-aminopropyl-9a-aza-9a-homoerythromycin A A mixture of 1.0 g (1.26 mmol) 9-deoxo-9-dihydro-9a-aza-9a-(γ-aminopropyl)-9a-homoerythromycin A and 0.17 g (1.3 mmol) of 1-naphtylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(1-naphtyl)thiocarbamoyl-γ-aminopropyl-9a-aza-9a-homoerythromycin A was obtained.

MS(ES$^+$)m/z=977.

EXAMPLE 6

9-Deoxo-9-dihydro-9a-N-[N'-(2-trifluoromethyl)phenylcarbamoyl-γ-aminopropyl]-9a-aza-9a-homoerythromycin A A mixture of 1.0 g (1.26 mmol) 9-deoxo-9-dihydro-9a-aza-9a-(γ-aminopropyl)-9a-homoerythromycin A and 0.24 g (1.3 mmol) of 2-(trifluoromethyl)phenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(2-trifluoromethylphenyl)carbamoyl-γ-aminopropyl]-9a-aza-9a-homoerythromycin A was obtained.

MS(ES$^+$)m/z=979.

EXAMPLE 7

9-Deoxo-9-dihydro-9a-N-[N'-(3-phenylpropyl)thiocarbamoyl-γ-aminopropyl]-9a-aza-9a-homoerythromycin A A mixture of 1.0 g (1.26 mmol) 9-deoxo-9-dihydro-9a-aza-9a-(γ-aminopropyl)-9a-homoerythromycin A and 0.22 g (1.3 mmol) of 3-phenylpropylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(3-phenylpropyl)thiocarbamoyl-γ-aminopropyl]-9a-aza-9a-homoerythromycin A was obtained.

MS(ES$^+$)m/z=969.

EXAMPLE 8

9-Deoxo-9-dihydro-9a-N-[N'-(β-phenylethyl)carbamoyl-γ-aminopropyl]-9a-aza-9a-homoerythromycin A A mixture of 1.0 g (1.26 mmol) 9-deoxo-9dihydro-9a-aza-9a-(γ-aminopropyl)-9a-homoerythromycin A and 0.21 g (1.3 mmol) of β-phenylethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(β-phenylethyl)carbamoyl-γ-aminopropyl]-9a-aza-9a-homoerithromycin A was obtained.

MS(ES$^+$)m/z=979.

EXAMPLE 9

9-Deoxo-9-dihydro-9a-N-(N'-ethoxycarbonylmethylcarbamoyl-γ-aminopropyl)-9a-aza-9a-homoerithromycin A A mixture of 1.0 g (1.26 mmol) 9-deoxo-9-dihydro-9a-aza-9a-(γ-aminopropyl)-9a-homoerithromycin A and 0.16 g (1.3 mmol) of ethoxycarbonylmethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-(N'-ethoxy-carbonylmethylcarbamoyl-γ-aminopropyl)-9a-aza-9a-homoerithromycin A was obtained.

MS(ES$^+$)m/z=921.

EXAMPLE 10

9-Deoxo-9-dihydro-9a-N-{N'-[1-(1-naphtyl)ethylcarbamoyl-γ-aminopropyl}-9a-aza-9a-homoerithromycin A A mixture of 1.0 g (1.26 mmol) 9-deoxo-9-dihydro-9a-aza-9a-(γ-aminopropyl)-9a-homoerithromycin A and 0.25 g (1.3 mmol) of 1-(1-naphtyl)ethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-{N'-[1-(1-naphtyl)ethylcarbamoyl-γ-aminopropyl}-9a-aza-9a-homoerithromycin A was obtained.

MS(ES$^+$)m/z=989.

EXAMPLE 11

9-Deoxo-9-dihydro-9a-N-[N'-(3,4,5-trimethoxyphenyl)carbamoyl-γ-aminopropyl]-9a-aza-9a-homoerithromycin A A mixture of 1.0 g (1.26 mmol) 9-deoxo-9-dihydro-9a-aza-9a-(γ-aminopropyl)-9a-homoerithromycin A and 0.26 g (1.3 mmol) of 3,4,5-trimethoxyphenylisocyanate in 10 ml dry toluene was stirred for 30 minutes at room temperature to complete the reaction. The crystals of the crude product were filtered, wherefrom by chromatography on sillica gel column using the solvent system methylene-chloride:: methanol:ammonia=90:9:1.5, pure 9-deoxo-9-dihydro-9a-N-[N'-(3,4,5-trimethoxyphenyl)carbamoyl-γ-aminopropyl]-9a-aza-9a-homoerithromycin A was obtained.

MS(ES$^+$)m/z=1001.

EXAMPLE 12

9-Deoxo-9-dihydro-9a-N-[N'-(2-naphtyl)carbamoyl-γ-aminopropyl]-9a-aza-9a-homoerithromycin A A mixture of 1.0 g (1.26 mmol) 9-deoxo-9-dihydro-9a-aza-9a-(γ-aminopropyl)-9a-homoerithromycin A and 0.23 g (1.3 mmol) of 2-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(2-naphtyl)carbamoyl-γ-aminopropyl]-9a-aza-9a-homoerithromycin A was obtained.

MS(ES$^+$)m/z=961.

EXAMPLE 13

9-Deoxo-9-dihydro-9a-N-[N'-(2,4-dichlorophenyl)carbamoyl-γ-aminopropyl]-9a-aza-9a-homoerithromycin A A mixture of 1.0 g (1.26 mmol) 9-deoxo-9-dihydro-9a-aza-9a-(γ-aminopropyl)-9a-homoerithromycin A and 0.23 g (1.3 mmol) of 2,4-dichlorophenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(2,4-dichlorophenyl)carbamoyl-γ-aminopropyl]-9a-aza-9a homoerithromycin A was obtained.

MS(ES$^+$)m/z=979.

EXAMPLE 14

5-O-Desosaminyl-9-deoxo-9-dihydro-9a-N-(N'-isopropylcarbamoyl-γ-aminopropyl)-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.13 g (1.57 mmol) of isopropylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-(N'-isopropylcarbamoyl-γ-aminopropyl)-9a-aza-9a-homoerithronolide A was obtained.

MS(ES$^+$)m/z=719.

EXAMPLE 15

5-O-Desosaminyl-9-deoxo-9-dihydro-9a-N-[N'-(1-naphtyl)carbamoyl-γ-aminopropyl]-9a-aza-9-a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.13 g (1.57 mmol) of 1-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(1-naphtyl)carbamoyl-γ-aminopropyl]-9a-aza-9a-homoerithronolide A was obtained.

MS(ES$^+$)m/z=803.

EXAMPLE 16

5-O-Desosaminyl-9-deoxo-9-dihydro-9a-N-(N'-benzylcarbamoyl-γ-aminopropyl)-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.21 g (1.57 mmol) of benzylisocyanate in 10 ml dry toluene was stirred for 30 minutes at room temperature to complete the reaction. The crystals of the crude product were filtered, wherefrom by chromatography on sillica gel column using the solvent system:methylene-chloride:methanol:ammonia=90:20:1.5, pure 5-O-desosaminyl-9-deoxo-9-dihydro-9a-N-(N'-benzylcarbamoyl-γ-aminopropyl)-9a-aza-9a-homoerithronolide A was obtained.

MS (ES$^+$)m/z=767.

EXAMPLE 17

5-O-Desosaminyl-9-deoxo-9-dihydro-9a-N-(N'-benzylthiocarbamoyl-γ-aminopropyl)-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.24 g (1.57 mmol) of benzylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-(N'-benzylthiocarbamoyl-γ-aminopropyl)-9a-aza-9a-homoerithronolide A was obtained.

MS(ES$^+$)m/z=783.

EXAMPLE 18

5-O-Desosaminyl-9-deoxo-9-dihydro-9a-N-[N'-(1-naphtyl)thiocarbamoyl-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.29 g (1.57 mmol) of 1-naphtylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(1-naphtyl)thiocarbamoyl-γ-aminopropyl]-9a-aza-9a-homoerithronolide A was obtained.

MS(ES$^+$)m/z=819.

EXAMPLE 19

5-O-Desosaminyl-9-deoxo-9-dihydro-9a-N-[N'-(2-(trifluoromethyl)phenylcarbamoyl)-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.30 g (1.57 mmol) of 2-(trifluoromethyl)phenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(2-(trifluoromethyl)phenylcarbamoyl-γ-aminopropyl]-9a-aza-9a-homoerithronolide A was obtained.

MS(ES$^+$)m/z=821.

EXAMPLE 20

5-O-Desosaminyl-9-deoxo-9-dihydro-9a-N-[N'-(3-phenylpropyl)thiocarbamoyl-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.28 g (1.57 mmol) of 3-phenylpropylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(3-phenylpropyl)thiocarbamoyl-γ-aminopropyl]-9a-aza-9a-homoerithronolide A was obtained.

MS(ES$^+$)m/z=811.

EXAMPLE 21

5-O-Desosaminyl-9-deoxo-9-dihydro-9a-N-[N'-(β-phenylethyl)thiocarbamoyl-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.26 g (1.57 mmol) of β-phenylethylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-phenylethyl)thiocarbamoyl-γ-aminopropyl]-9a-aza-9a-homoerithonolide A was obtained.

MS(ES$^+$)m/z=797.

EXAMPLE 22

5-O-Desosaminyl-9-deoxo-9-dihydro-9a-N-(N'-ethoxykarbonylmethyl-carbamoyl-γ-aminopropyl)-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.20 g (1.57 mmol) of ethoxykarbonylmethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-(N'-ethoxykarbonylmethylcarbamoyl-γ-aminopropyl)-9a-aza-9a-homoerithronolideA was obtained.

MS(ES$^+$)m/z=763.

EXAMPLE 23

5-O-Desosaminyl-9-deoxo-9-dihydro-9a-N-[N'-(2-naphtyl)carbamoyl-γ-aminopropyl]-9a-aza-9a-homo-erithonolide A A mixture of 1.0 g (1.57 mmol) 5-O-desosaminyl-9-deoxo-9-dihydro-9a-N-(γ-aminopropyl)-9a-aza-homoerithronolide A and 0.27 g (1.57 mmol) of 2-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(2-naphtyl)carbamoyl-γ-aminopropyl]-9a-aza-9a-homoerithronolideA was obtained.

MS(ES$^+$)m/z=803.

EXAMPLE 24

5-O-Desosaminyl-9-deoxo-9-dihydro-9a-N-{N'-[1-(1-naphtyl)ethyl]carbamoyl-γ-aminopropyl}-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.31 g (1.57 mmol) of 1-(1-naphtyl)ethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-{N'-[1-(1-naphtyl)ethyl]carbamoyl-γ-aminopropyl}-9a-aza-9a-homo-erithronolideA was obtained.

MS (ES$^+$)m/z=831.

EXAMPLE 25

5-O-Desosaminyl-9-deoxo-9-dihydro-9a-N-[N'-(3,4,5-trimethoxyphenyl)-carbamoyl-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.31 g (1.57 mmol) of 3,4,5-trimethoxyphenylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(3,4,5-trimethoxyphenyl)carbamoyl-γ-aminopropyl]-9a-aza-9a-homoerithronolide A was obtained.

MS(ES$^+$)m/z=843.

EXAMPLE 26

5-O-Desosaminyl-9-deoxo-9-dihydro-9a-N-[N'-(2,4-dichlorophenyl)carbamoyl-γ-aminopropyl]-9a-aza-9a-homoerithronolide A A mixture of 1.0 g (1.57 mmol) 5-O-desosaminyl-9-deoxo-9-dihydro-9a-N-(γ-aminopropyl)-9a-aza-homoerithronolide A and 0.31 g (1.57 mmol) of 2,4-dichlorophenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(3,4,5-trimethoxyphenyl)carbamoyl-γ-aminopropyl]-9a-aza-9a-homoerithronolide A was obtained.

MS(ES$^+$)m/z=821.

EXAMPLE 27

9-Deoxo-9-dihydro-9a-N-[N'-(β-cyanoethyl)-N'-isopropylcarbamoyl-γ-aminopropyl]-9a-aza-9a-homorithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.06 g (0.591 mmol) of isopropylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-isopropylcarbamoyl-γ-aminopropyl]-9a-aza-9a-homoerithromycin A was obtained.

MS(ES$^+$)m/z=931.

EXAMPLE 28

9-Deoxo-9-dihydro-9a-N-[N'-(β-cyanoethyl)-N'-(1-naphtyl)carbamoyl-γ-aminopropyl]-9a-aza-9a-homo-erithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.11 g (0.591 mmol) of 1-naphtylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(1-naphtyl)carbamoyl-γ-aminopropyl]-9a-aza-9a-homoerithromycin A was obtained.

MS(ES$^+$)m/z=.

EXAMPLE 29

9-Deoxo-9-dihydro-9a-N-[N'-(β-cyanoethyl)-N'-benzylcarbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.08 g (0.591 mmol) of benzylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-benzylcarbamoyl-γ-aminopropyl]-9a-aza-9a-homoerithromycin A was obtained.

MS(ES$^+$)m/z=931.

EXAMPLE 30

9-Deoxo-9-dihydro-9a-N-[N'-(β-cyanoethyl)-N'-benzylthiocarbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.09 g (0.591 mmol) of benzylisothiocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-benzylthiocarbamoyl-γ-aminopropyl]-9a-aza-9a-homoerithromycin A was obtained.

MS(ES$^+$)m/z=995.

EXAMPLE 31

9-Deoxo-9-dihydro-9a-N-[N'-(β-cyanoethyl)-N'-(1-naphtyl)thiocarbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.12 g (0.591 mmol) of 1-naphtylisothiocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(1-naphtyl)thiocarbamoyl-γ-aminopropyl]-9a-aza-9a-homoerithromycin A was obtained.

MS(ES$^+$)m/z=1029.

EXAMPLE 32

9-Deoxo-9-dihydro-9a-N-[N'-(β-cyanoethyl)-N'-(2-(trifluoromethyl)phenyl)carbamoyl-γ-aminopropyl]-9a-aza-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.08 g (0.591 mmol) of 2-(trifluoromethyl)phenylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(2-(trifluoromethyl)phenyl)carbamoyl-γ-aminopropyl]-9a-aza-homoerithromycin A was obtained.

MS(ES$^+$)m/z=1033.

EXAMPLE 33

9-Deoxo-9-dihydro-9a-N-[N'-(β-cyanoethyl)-N'-(3-phenylpropyl)carbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.10 g (0.591 mmol) of 3-phenylpropylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(3-phenylpropyl)carbamoyl-γ-aminopropyl]-9a-aza-9a-homoerithromyci A was obtained.

MS(ES$^+$)m/z=1022.

EXAMPLE 34

9-Deoxo-9-dihydro-9a-N-[N'-(β-cyanoethyl)-N'-(β-phenylethyl)thiocarbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.10 g (0.591 mmol) of β-phenylethylisothiocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(β-phenylethyl)thiocarbamoyl-γ-aminopropyl]-9a-aza-9a-homoerithromycin A was obtained.

MS(ES$^+$)m/z=1008.

EXAMPLE 35

9-Deoxo-9-dihydro-9a-N-[N'-(β-cyanoethyl)-N'-ethoxycarbonylmethyl-carbamoyl]-γ-aminopropyl]-9a-aza-9a-homoerithromycin A A mixture of 0.5 g (0.591 mmol) 9-deoxo-9-dihydro-9a-N-[N-(β-cyanoethyl)-γ-aminopropyl]-9a-aza -9a-homoerithromycin A and 0.10 g (0.591 mmol) of ethoxycarbonylmethylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-ethoxycarbonylmethylcarbamoyl]-γ-aminopropyl]-9a-aza-9a-homoerithromycin A was obtained.

MS(ES$^+$)m/z=974.

EXAMPLE 36

9-Deoxo-9-dihydro-9a-N-{N'-(β-cyanoethyl)-N'-[1-(1-naphtyl)ethyl]carbamoyl-γ-aminopropyl}-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.11 g (0.591 mmol) of 1-(1-naphtyl)ethylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-{N'-(β-cyanoethyl)-N'-[1-(1-naphtyl)ethyl]carbamoyl-γ-aminopropyl}-9a-aza-9a-homoerithromycinA was obtained.

MS(ES$^+$)m/z=1042.

EXAMPLE 37

9-Deoxo-9-dihydro-9a-N-[N'-(β-cyanoethyl)-N'-(3,4,5-trimethoxyphenyl)carbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.12 g (0.591 mmol) of 3,4,5-trimethoxyphenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(3,4,5-trimethoxyphenyl)carbamoyl-γ-aminopropyl]-9a-aza-9a-homoerithromycin A was obtained.

MS(ES$^+$)m/z=1053.

EXAMPLE 38

9-Deoxo-9-dihydro-9a-N-[N'-(β-cyanoethyl)-N'-(2-naphtyl)carbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.11 g (0.591 mmol) of 2-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(2-naphtyl)carbamoyl-γ-aminopropyl]-9a-aza-9a-homoerithromycin A was obtained.

MS(ES$^+$)m/z=1014.

EXAMPLE 39

9-Deoxo-9-dihydro-9a-N-[N'-(β-cyanoethyl)-N'-(2,4-dichlorophenyl)carbamoyl-γ-aminopropyl]-9a-aza-9a-homoerithromycin A A mixture of 0.5 g (0.591 mmol) 9-deoxo-9-dihydro-9a-N-[N'-(β-cyanoethyl)-γ-aminopropyl]-9a-aza-9a-homoerithromycin A and 0.11 g (0.591 mmol) of 2-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:9:1.5, pure 9-deoxo-9-dihydro-9a-N-[N'-(β-cyanoethyl)-N'-(2,4-dichlorophenyl)carbamoyl-γ-aminopropyl]-9a-aza-9a-homoerithromycin A was obtained.

MS(ES$^+$)m/z=1033.

EXAMPLE 40

5-O-Desosaminyl-9-deoxo-9-dihydro-9a-N-[N'-(β-cyanoethyl)-N'-isopropylcarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.06 g (0.728 mmol) of isopropylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-isopropylcarbamoyl-γ-aminopropyl]-9a-aza-9a-homoerithronolide A was obtained.

MS(ES$^+$)m/z=771.

EXAMPLE 41

5-O-Desosaminyl-9-deoxo-9-dihydro-9a-N-[N'-(β-cyanoethyl)-N'-(1-naphtyl)carbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.12 g (0.728 mmol) of 1-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(1-naphtyl)carbamoyl-γ-aminopropyl]-9a-aza-9a-homoerithronolide A was obtained.

MS(ES$^+$)m/z=855.

EXAMPLE 42

5-O-Desosaminyl-9-deoxo-9-dihydro-9a-N-[N'-(β-cyanoethyl)-N'-benzylcarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.10 g (0.728 mmol) of benzylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-benzylcarbamoyl-γ-aminopropyl]-9a-aza-9a-homoerithronolide A was obtained.

MS(ES$^+$)m/z=819.

EXAMPLE 43

5-O-Desosaminyl-9-deoxo-9-dihydro-9a-N-[N'-(β-cyanoethyl)-N'-benzylthiocarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.11 g (0.728 mmol) of benzylisocyanate in 10 ml dry toluene was stirred for 30 minutes at room temperature to complete the reaction. The crystals of the crude product were filtered, wherefrom by chromatography on silica gel column using the solvent system methylene-chloride:methanol:ammonia=90:20:1.5, pure 5-O-desosaminyl-9-deoxo-9-dihydro-9a-N-[N'-(β-cyanoethyl)-N'-benzylthiocarbamoyl-γ-aminopropyl]-9a-aza-9a-homoerithronolide A was obtained.

MS(ES$^+$)m/z=835.

EXAMPLE 44

5-O-Desosaminyl-9-deoxo-9-dihydro-9a-N-[N'-(β-cyanoethyl)-N'-(1-naphtyl)thiocarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.14 g (0.728 mmol) of 1-naphtylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(1-naphtyl)thiocarbamoyl-γ-aminopropyl]-9a-aza-9a-homoerithronolide A was obtained.

MS(ES$^+$)m/z=855.

EXAMPLE 45

5-O-Desosaminyl-9-deoxo-9-dihydro-9a-N-[N'-(β-cyanoethyl)-N'-(2-(trifluoromethyl)phenyl)carbamoyl -γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.14 g (0.728 mmol) of 2-(trifluoromethyl)phenylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(2-(trifluoromethyl)-phenylcarbamoyl-γaminopropyl]-9a-aza-9a-homoerithronolide A was obtained.

MS(ES$^+$)m/z=873.

EXAMPLE 46

5-O-Desosaminyl-9-deoxo-9-dihydro-9a-N-[N'-(β-cyanoethyl)-N'-(3-phenylpropyl)thiocarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.13 g (0.728 mmol) of 3-phenylpropylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(3-cyanoethyl)-N'-(3-phenylpropyl)thiocarbamoyl-γ-aminopropyl]-9a-aza-9a-homoerithronolide A was obtained.

MS(ES$^+$)m/z=863.

EXAMPLE 47

5-O-Desosaminyl-9-deoxo-9-dihydro-9a-N-[N'-(β-cyanoethyl)-N'-(β-phenylethyl)thiocarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.12 g (0.728 mmol) of β-phenylethylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(β-phenylethyl)thiocarbamoyl-γ-aminopropyl]-9a-aza-9a-homoerithronolide A was obtained.

MS(ES$^+$)m/z=.

EXAMPLE 48

5-O-Desosaminyl-9-deoxo-9-dihydro-9a-N-[N'-(β-cyanoethyl)-N'-ethoxy-carbonylmethylcarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.09 g (0.728 mmol) of β-phenylethylisothiocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-ethoxycarbonylmethylcarbamoyl-γ-aminopropyl]-9a-aza-9a-homoerithronolide A was obtained.

MS(ES$^+$)m/z=815.

EXAMPLE 49

5-O-Desosaminyl-9-deoxo-9-dihydro-9a-N-[N'-(β-cyanoethyl)-N'-(2-naphtyl)carbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.12 g (0.728 mmol) of 2-naphtylisocyanate in 10 ml dry toluene was stirred for 30 minutes at room temperature to complete the reaction. The crystals of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(2-naphtyl)carbamoyl-γ-aminopropyl]-9a-aza-9a-homoerithronolideA was obtained.

MS(ES$^+$)m/z=855.

EXAMPLE 50

5-O-Desosaminyl-9-deoxo-9-dihydro-9a-N-[N'-(β-cyanoethyl)-N'-[1-(1-naphtyl)ethylcarbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.15 g (0.728 mmol) of 1-(1-naphtyl)ethylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-[1-(1-naphtyl)ethyl)carbamoyl-γ-aminopropyl]-9a-aza-9a-homoerithronolide A was obtained.

MS(ES$^+$)m/z=883.

EXAMPLE 51

5-O-Desosaminyl-9-deoxo-9-dihydro-9a-N-[N'-(β-cyanoethyl)-N'-(3,4,5-trimethoxyphenyl)carbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.14 g (0.728 mmol) of 3,4,5-trimethoxyphenylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(3,4,5-trimethoxyphenyl)carbamoyl-γ-aminopropyl]-9a-aza-9a-homoerithronolide A was obtained.

MS(ES$^+$)m/z=895.

EXAMPLE 52

5-O-Desosaminyl-9-deoxo-9-dihydro-9a-N-[N'-(β-cyanoethyl)-N'-(2,4-dichlorophenyl)carbamoyl-γ-aminopropyl]-9a-aza-9a-homoerithronolide A A mixture of 0.5 g (0.728 mmol) 5-O-desosaminyl-9-deoxo-9-dihydro-9a-N-(γ-aminopropyl)-9a-aza-homoerithronolide A and 0.14 g (0.728 mmol) of 2,4-dichlorophenylisocyanate in 10 ml dry toluene was stirred for 30 minutes at room temperature to complete the reaction. The crystalls of the crude product were filtered, wherefrom by chromatography on sillica gel column using the solvent system methylene-chloride:methanol:ammonia=90:20:1.5, pure 5-O-desosaminyl-9-deoxo-9-dihydro-9a-N-[N'-(β-cyanoethyl)-N'-(2,4-dichlorophenyl)carbamoyl-γ-aminopropyl] 9a-aza-9a-homoerithronolide A was obtained.

MS(ES$^+$)m/z=874.

The invention claimed is:

1. A compound of formula 1,

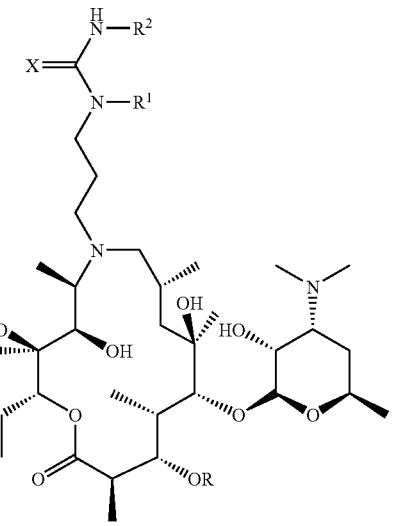

wherein R represents H or cladinosyl moiety, $R^1$ represents H or β-cyanoethyl moiety, $R^2$ represents isopropyl, 1-naphtyl, 2-naphtyl, benzyl, 2-(trifluoromethyl)phenyl, 3-phenylpropyl, β-phenylethyl, ethoxycarbonyl-methyl, 1-(1-naphtyl)ethyl, 3,4,5-trimethoxyphenyl or a 2,4-dichlorophenyl group, and X represents O or S, or a pharmaceutically acceptable acid addition salt thereof.

2. A compound according to claim 1, characterized in that $R^1$ represents H, $R^2$ represents isopropyl group and X is O.

3. A compound according to claim 1, characterized in that $R^1$ represents H, and $R^2$ represents 1-naphthyl group and X is O.

4. A compound according to claim 1, characterized in that $R^1$ represents H and $R^2$ represents 2-naphtyl group and X is O.

5. A compound according to claim 1, characterized in that $R^1$ represents H and $R^2$ represents benzyl group and X is O.

6. A compound according to claim 1, characterized in that $R^1$ represents H and $R^2$ represents 2-(trifluoromethyl) phenyl group and X represents O.

7. A compound according to claim 1, characterized in that $R^1$ represents H and $R^2$ represents 3-phenylpropyl group and X is S.

8. A compound according to claim 1, characterized in that $R^1$ represents H and $R^2$ represents 3-phenylethyl group and X is S.

9. A compound according to claim 1, characterized in that $R^1$ represents H and $R^2$ represents ethoxycarbonylmethyl group and X is O.

10. A cornppvnd according to claim 1, characterized in that $R^1$ represents H and $R^2$ represents 1-(1-naphtyl)ethyl group and X is O.

11. A compound according to claim 1, characterized in that R¹ represents H and R² represents 3,4,5-trimethoxyphenyl group and X is O.

12. A compound according to claim 1, characterized in that R¹ represents H and R² represents 2,4-dichlorophenyl group and X is O.

13. A compound according to claim 1, characterized in that R¹ represents H and R² represents benzyl group or 1-naphtyl group and X is S.

14. A compound according to claim 1, characterized in that R¹ represents β-cyanoethyl group, R² represents 3-phenylpropyl group and X is S.

15. A compound according to claim 1, characterized in that R¹ represents β-cyanoethyl group, R² represents β-phenylethyl group and X is S.

16. A compound according to claim 1, characterized in that R¹ represents β-cyanoethyl group, R² represents 2,4-dichlorophenyl group and X is O.

17. Process for the preparation of a compound of formula 1,

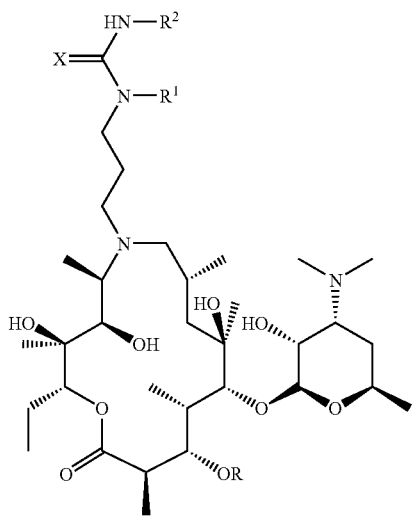

wherein R represents H or cladinosyl moiety,

R¹ represents H or β-cyanoethyl moiety,

R² represents isopropyl, 1-naphtyl, 2-naphtyl, benzyl, 2-(trifluoromethyl) phenyl, 3-phenylpropyl, β-phenylethyl, ethoxycarbonylmethyl, 1-(1-naphtyl) ethyl, 3,4,5-trimethoxyphenyl and 2,4-dichlorophenyl group, and X represents O or S, characterized in that a compound of formula 2,

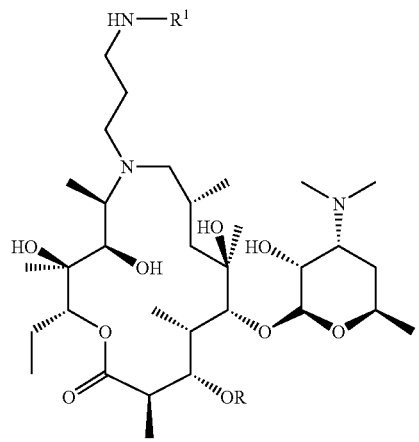

wherein R represents H or a cladinosyl group and

R¹ represents H or a β-cyanoethyl group is reacted with isocyanates or isothiocyanates of general formula 3

R²—N=C=X    3 wherein R² represents isopropyl, 1-naphtyl, 2-naphtyl, benzyl, 2-(trifluoromethyl) phenyl, 3-phenyipropyl, β-phenylethyl, ethoxycarbonyl-methyl, 1-(1-naphtyl)ethyl, 3,4,5-trimethoxyphenyl and or 2,4-dichlorophenyl group, and X represents O or S, in toluene, xylene or some others aprotic solvents at a temperature 0°-110° C. and then, if appropriate, to a reaction with inorganic or organic acids.

18. A Pharmaceutical compositions comprising a pharmaceutically acceptable carrier and an antibacterially effective amount of the a substance compound according to claim 1.

19. A method of treating bacterial infections in a mammal comprising administering to such mammal an antibacterially effective amount of a compound of formula 1 according to claim 1.

20. The method according to clam 19, wherein R¹ of a compound of formula 1 represents H.

21. The method according to claim 19, wherein R² of a compound of formula 1 represents a 1-naphthyl, 2-naphthyl, 1-(1-naphtyl)ethyl, or 2,4-dichlorophenyl group.

22. The method according to claim 19, wherein the mammal is a human.

* * * * *

UNITED STATES PATENT AND TRADEMARK OFFICE
CERTIFICATE OF CORRECTION

PATENT NO. : 7,342,000 B2
APPLICATION NO. : 10/538376
DATED : March 11, 2008
INVENTOR(S) : Nedjeljko Kujundzic, Mirjana Bukvic Krajacic and Karmen Brajsa It is certified that error appears in the above-identified patent and that said Letters Patent is hereby corrected as shown below:

In Column 22, line 59, "3" should read --β--
In Column 23, line 5, "dichiorophenyl" should read --dichlorophenyl--
In Column 24, line 36, "compositions" should read --composition--
In Column 24, line 38, "the" and "substance" should be deleted Signed and Sealed this Twenty-third Day of September, 2008

JON W. DUDAS
*Director of the United States Patent and Trademark Office*